United States Patent [19]

Wagner

[11] 3,959,723

[45] May 25, 1976

[54] LUMBER MOISTURE MEASUREMENT APPARATUS WHICH IS LESS SENSITIVE TO LUMBER MOVEMENT AND SPACING

[76] Inventor: Delmer W. Wagner, 392 Pine Grove Road, Rogue River, Oreg. 97537

[22] Filed: Sept. 13, 1974

[21] Appl. No.: 505,850

[52] U.S. Cl. .......................... 324/61 P; 324/61 QS; 324/61 QL
[51] Int. Cl.² .................................. G01R 27/26
[58] Field of Search ............ 324/61 R, 61 P, 61 QL, 324/61 QS, 9

[56] References Cited
UNITED STATES PATENTS

| | | | |
|---|---|---|---|
| 2,606,310 | 8/1952 | Baker | 324/61 R |
| 2,948,850 | 8/1960 | Ederer | 324/61 P |
| 3,009,101 | 11/1961 | Locher | 324/61 P |
| 3,450,988 | 6/1969 | Breen et al. | 324/61 R |
| 3,523,243 | 8/1970 | Wagner | 324/61 R |
| 3,523,246 | 8/1970 | Hall et al. | 324/61 R |

OTHER PUBLICATIONS

Kartashova et al., "Contactless Measurements of the Thickness of Plane Dielectrics," Meas. Tech. (USA) Vol. 15, 7-1972, pp. 1025-1027.

*Primary Examiner*—John K. Corbin
*Assistant Examiner*—Wm. H. Punter
*Attorney, Agent, or Firm*—Klarquist, Sparkman, Campbell, Leigh, Hall & Whinston

[57] ABSTRACT

Apparatus for measuring moisture in lumber and the like comprises a plurality of plates including at least one transmitting plate connected to a radio frequency generator, phase plates connected in circuit for providing an out of phase signal, and a receiver plate normally balanced to receive substantially zero signal input. Moist lumber next to the array of plates couples the radio frequency signal therealong and affects the balance of the system whereby the signal received at the receiver plate is in accordance with the moisture in the lumber.

8 Claims, 3 Drawing Figures

LUMBER MOISTURE MEASUREMENT APPARATUS WHICH IS LESS SENSITIVE TO LUMBER MOVEMENT AND SPACING

BACKGROUND OF THE INVENTION

This invention relates to apparatus for measuring the moisture content of material and particularly to such apparatus which has a spaced or non-contacting relationship with the material under test.

Most capacitor means for sensing the moisture content of material tend to be sensitive to the thickness of the material or the placement of the material relative to the capacitor plates. In apparatus according to my U.S. Pat. No. 3,523,243 granted Aug. 4, 1970, sensitivity to the thickness and placement of material is reduced by coupling radio frequency energy along the length of the material between offset or non-juxtaposed plates, while ground plates are interposed to "shunt out" some of the radio frequency signal when the material more closely approaches transmitting and receiving plates. While this equipment has the advantage of improved independence of material placement relative to capacitor plate means, the range of independence is found to be relatively close proximity to the capacitor plate apparatus which can result in damage to the apparatus if struck by material measured. It is also desired to provide apparatus having a greater range of independence due to movement of the material. Therefore, lumber or similar material can be accommodated having a greater degree of warp or irregularity without equipment damage and with enhanced accuracy of output indication.

SUMMARY OF THE INVENTION

According to the present invention, a moisture measuring apparatus comprises a plurality of conductor means disposed in facing relation to the material to be tested. This conductor means is coupled to radio frequency generator means in a first phase sense, while second conductor means are coupled to the generator means in an opposite or out of phase sense. A third conductor means is coupled to means for indicating the moisture in the material and the third conductor means is preferably coupled by additional circuitry to the radio frequency generator means for normally producing a null or other desired condition at the said means for indicating moisture.

It is found that the apparatus of the present invention in use provides immunity to position of the material under test at a greater distance from the testing apparatus than was the case in prior apparatus, and also provides a greater range of the immunity from material position. Not only is accuracy enhanced, but the testing apparatus can be located at a safer distance from the material tested.

It is accordingly an object of the present invention to provide improved apparatus for measuring the moisture content of material wherein said apparatus is disposed in spaced relation to the material.

It is another object of the present invention to provide improved apparatus for measuring the moisture content of material having enhanced immunity from material position relative to the aforesaid apparatus.

It is another object of the present invention to provide improved apparatus for measuring the moisture content of material wherein the spacing between the measuring apparatus and the material can be greater.

It is a further object to provide improved apparatus for measuring the moisture content of material wherein said apparatus is characterized by improved accuracy and adaptability.

The subject matter which I regard as my invention is particularly pointed out and distinctly claimed in the concluding portion of this specification. The invention, however, both as to organization and method of operation, together with further advantages and objects thereof, may best be understood by reference to the following description taken in connection with the accompanying drawings wherein like reference characters refer to like elements.

DRAWINGS

DETAILED DESCRIPTION

Figure 1:
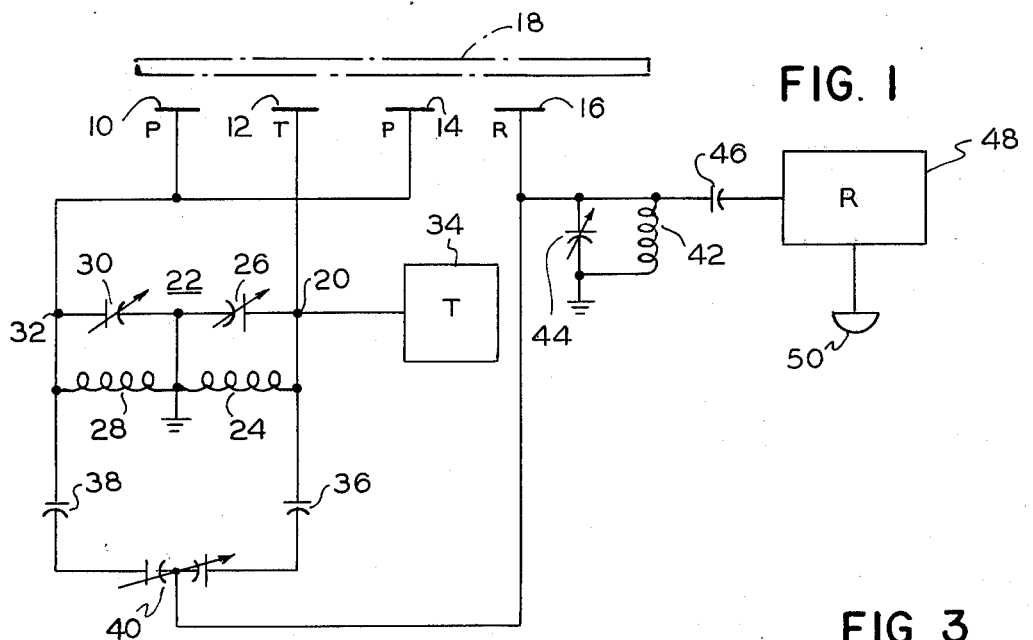
FIG. 1 is a schematic diagram of the apparatus according to the present invention.

Referring to the drawings and particularly to FIG. 1, the apparatus according to the present invention comprises a plurality of conductor plate means 10, 12, 14 and 16 located in that order, in offset relation to each other and in substantial juxtaposition with material 18, the moisture content of which is to be ascertained. Typically, the material comprises lumber in a sawmill or the like.

For convenience of reference, a center plate 12 will be designated a transmitting plate while plates 10 and 14 disposed on either side thereof will be referred to as phase plates. A receiving plate, 16 is located on one side or the other of the array of plates 10, 12, 14, and plate 16 is typically spaced a little further from the array 10, 12, 14 than the spacing of the plates within the array. Transmitting plate 12 is connected to a first terminal end 20 of a double tank circuit 22 comprising inductance 24 shunted by variable capacitor 26 disposed between terminal 20 and ground, and an inductance 28 shunted by variable capacitor 30 interposed between ground and phase terminal 32. Both inductor-capacitor combinations are tuned to the transmitting frequency of a radio frequency generator 34 connected to terminal 20. Inductances 24 and 28 are inductively coupled whereby the voltage at point 32 is 180° out of phase with the voltage at point 20.

Terminals 20 and 32 are respectively coupled by means of capacitors 36 and 38 to opposite terminals of a double or split stator capacitor 40 having its center point connected to receiving plate 16. Receiving plate 16 is shunted to ground by a parallel tuned circuit, tuned to the transmitting frequency, composed of inductance 42 in parallel with capacitor 44, with the receiving plate further being coupled via capacitor 46 to receiving circuitry 48 adapted for providing an output signal for operating alarm 50. The transmitting and receiving circuitry is suitably substantially the same as disclosed in my U.S. Pat. No. 3,523,243 granted Aug. 4, 1970.

Considering operation of the circuit, it will be seen the plate 12 on the one hand, and plate 10, 14 on the other, are provided with out of phase signals which would tend to induce oppositely phased signals in plate 16 by capacitive coupling. To insure a null or other desired condition for plate 16, the same is connected via capacitor 40 whereby the net result of the transmitted signal at plate 16 can be adjusted to zero in the absence of a board or other material 18 located adjacent the plates. When such a board is positioned adjacent the plates, the nulled condition at plate 16 is thrown out of balance, and the receiver 48 receives an input. The extent of the signal reaching receiver 48 will be dependent upon the moisture contained in board 18, and a threshold may be set for the operation of alarm 50 when a predetermined level of moisture is exceeded.

The configuration according to the present invention has the advantage of being relatively less sensitive to the positioning of a board or material 18 than are various prior art capacitive moisture detectors. This insensitivity results from the fact that as material 18 more closely approaches plates 10, 12 and 14, the effect will be one of shunting out the signal between plates 12 and 14 for example, or the signal between plates 12 and 10. This counterbalances the effect of the stronger coupling of the signal into material 18 brought about by the mere closer proximity of material 18 to the plates. The phase plates 10 and 14 thus have an effect somewhat similar to that of the grounding plates disposed between transmitting and receiving plates in my aforementioned U.S. Pat. No. 3,523,243. However, the apparatus according to the present invention produces this relative immunity to positioning of material 18 at further distances from the array of plates. By providing an active signal on both the transmitting and phase plates relative to their environment, it appears the field resulting from the plates can be manipulated at higher levels. The effect and advantageous spacing of the phase plates can be adjusted through adjustment of the relative voltage placed on plates 10 and 14, as by means hereinafter more fully described.

With the present invention the nominal spacing of the wood or other material to plates 10, 12, 14, 16 is arranged to be approximately one inch, but variation of this spacing is tolerated, due to warp of the board and the like, without incorrectly influencing the moisture measurements due to improper spacing. For example, the spacing can vary one-fourth of an inch either way without substantial change in the moisture reading or alarm output for a board having a given moisture content. A closer nominal spacing was ordinarily required with the apparatus according to my prior U.S. Pat. No. 3,523,243.

It is postulated that when material 18 is brought into the proximity of the plates 10, 12, 14, 16 the receiving plate 16 receives a greater signal along material 18 from one of the phase plates 10 or 12 than would be the case in the absence of material 18. It will be noted that since the plates are disposed along the material 18, the coupling path between plates is primarily longitudinal of the material, with the plates all being offset with respect to one another, that is non-juxtaposed. This arrangement also enhances the immunity from thickness and positioning of material 18 according to the apparatus of the present invention, so that the output is an indication of moisture content.

Figure 2:
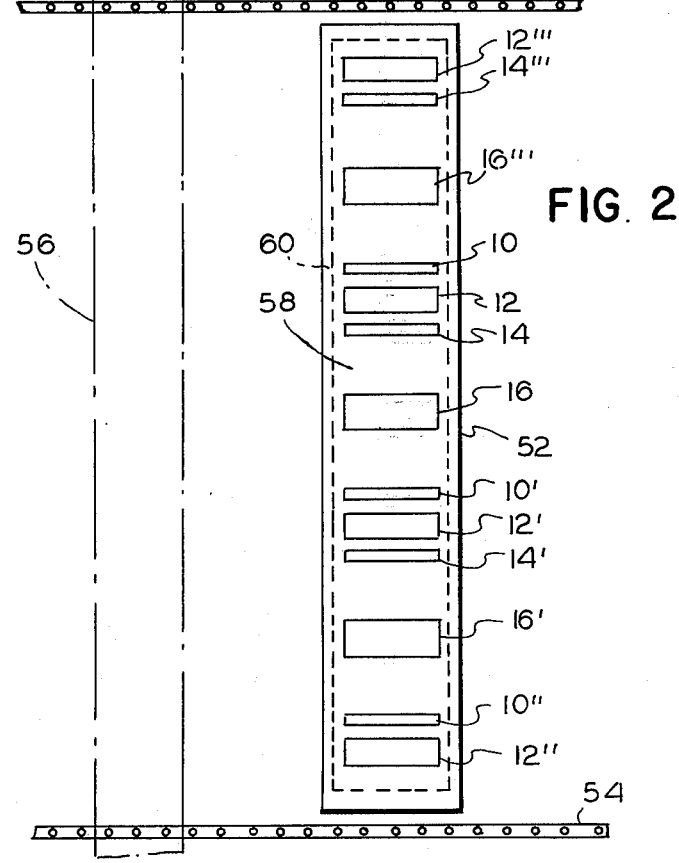
FIG. 2 is a plan view illustrating the mechanical placement of apparatus according to the present invention.

FIG. 2 illustrates the physical arrangement of an embodiment according to the present invention wherein a plurality of plate arrays are disposed along the top of the single support cabinet 52 located between conveyor chains 54 upon which a board 56 is conveyed, in the direction indicated, over the top of cabinet 52 at a spacing of approximately one inch from the plates. Plates 10, 12, 14 and 16 are illustrated in FIG. 2, along with adjoining arrays of plates having sequentially primed reference numerals. "Half arrays" of transmitting and phase plates 12″, 10″ and 12‴, 14‴ are located at the ends of the cabinet 52. In a typical instance, the cabinet 52 is approximately 3 inches wide by 20 inches long and the receiving plates, e.g. plate 16, are approximately 1⅛ inches wide by 2½ inches long. Transmitting plate 12 is about 1 inch wide while phase plates 10 and 14 are ½ inch wide, with the length of these plates being the same as that of plate 16. The various plates suitably comprise printed or etched conductors on a circuit board 58 composed of epoxy glass and forming the top of the cabinet 52. An underlying grounded edge conductor 60 is located on the underside of circuit board 58 and is grounded to the flange of the cabinet 52. Cabinet 52 is suitably formed of metal and contains the circuitry according to FIG. 1. Preferably the printed circuit board 58 including the plate arrays is covered over with a layer of polyethylene plastic having a thickness between one-sixteenth inch and one-eight inch. In installations where a large conveyor is utilized, having a plurality of further chains 54, a further plurality of moisture detectors housed in cabinets 52 may be located between adjacent chain runs in substantial alignment with the one illustrated.

Although the apparatus according to the present invention illustrates a board passing over the plate array in a sideways direction, it is clear that such board can be passed over the equipment in a lengthways direction if so desired.

Figure 3:
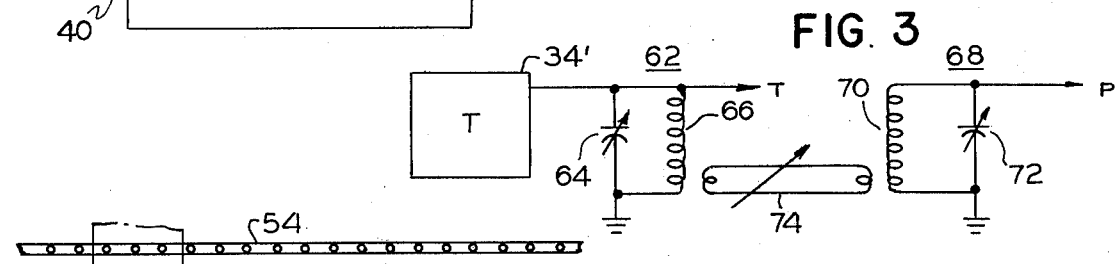
FIG. 3 is a schematic diagram according to an alternative embodiment of the present invention.

FIG. 3 illustrates an alternative circuit according to the present invention employing a radio frequency generator 34′ having its output connected to one end of a tank circuit 62 composed of a capacitor 64 and an inductance 66 interposed between the generator output and ground. Terminal T is connected to the transmitting plates of the plate array. Tank circuit 62 is tuned to the transmitting frequency. A further tank circuit 68, composed of inductance 70 shunted by capacitor 72 interposed between terminal P and ground, is also tuned to the same frequency, and is coupled by means of link coupling means 74 to the tank circuit 62. Alternatively, a link winding coupled to inductance 66 is connected directly across inductance 70. The coupling or polarity of the coils is arranged so that terminal P is out of phase with terminal T. Terminal P is connected to the phase plates in the plate arrays, and the voltage at terminal P is adjusted by means of adjusting the degree of coupling of link 74. In general, it is desirable that the voltage at terminal P times the area of both plates 10 and 14 be the same as the voltage at terminal T times the area of plate 12. Also, capacitive coupling may be employed between terminals T and P and the respective plates if so desired. Other means of adjusting the voltage at phase plates will occur to those skilled in the art. By means of adjusting the relative voltage at terminal P the penetration in an upwards direction into material 18 and the region of substantial immunity from spacing of the wood can be adjusted. Moreover, the side effect or fringe effect can be adjusted so that the array of plates is primarily responsive only to material directly thereover, or so that side cutoff is at a given lateral distance relative to the array of plates. Of course, the upward penetration of the field in the material 18 and the side cutoff of the field are interrelated.

The apparatus according to the present invention is advantageously placed underneath the conveyor system at an increased spacing from the lumber as compared with prior devices. Therefore, less interference with the conveying system and less likelihood of damage to the equipment is likely to result. However, it will be apparent that the plate arrays can be disposed above the material to be tested if so desired, or plates of the arrays can be alternately located on opposite sides of the material, preferably with plates of a similar kind or connection being disposed in offset or non-juxtaposed relation for maximum transmission of the signal along the moisture path in the wood rather than directly across a cross section of the wood.

While the detecting equipment is illustrated as sounding an alarm, the moisture content of various boards can be metered or recorded, if so desired, according to the amplitude of the output signal from receiver 48. Also, counting equipment can be employed for counting the boards having different levels of moisture.

While I have shown and described several embodiments of my invention, it will be apparent to those skilled in the art that many changes and modifications may be made without departing from my invention in its broader aspects. I therefore intend the appended claims to cover all such changes and modifications as fall within the true spirit and scope of my invention.

I claim:

1. Apparatus for measuring the moisture content of material, said apparatus comprising:
   first conductor means disposed in facing relation to said material,
   second conductor means disposed in facing relation to said material,
   and third conductor means disposed in facing relation to said material,
   radio frequency generator means coupled for energizing said first and second conductor means in predetermined out of phase relation,
   and means responsive to the field at said third conductor means for indicating moisture in said material,
   wherein said first, second and third conductor means comprise an array which includes a said first conductor means a said second conductor means and a said third conductor means disposed in order and in offset relation to one another, while being in spaced relation to said material, said third conductor means being disposed on the remote side of said second conductor means from said first conductor means.

2. The apparatus according to claim 1 wherein said conductors comprise plates disposed in facing relation to the path of said material for substantially simultaneously facing said material.

3. The apparatus according to claim 1 further including balancing means for coupling said third conductor means to said first and second conductor means for normally balancing the signals of said first and second conductor means at said third conductor means.

4. The apparatus according to claim 1 wherein said radio frequency generator means comprises tank circuitry having oppositely phased signal points coupled respectively to said first and second conductor means.

5. The apparatus according to claim 1 wherein said means responsive to the field of said third conductor means comprises radio frequency receiving circuitry.

6. The apparatus according to claim 1 further comprising balancing means for coupling said third conductor means with said first and second conductor means, said balancing means comprising a balancing capacitor having three capacitively related terminals coupled respectively to said first, second and third conductor means for adjusting the relative capacitance between said third conductor means and said first and second conductor means.

7. Apparatus for measuring the moisture content of material, said apparatus comprising:
   first conductor means disposed in facing relation to said material,
   second conductor means disposed in facing relation to said material,
   and third conductor means disposed in facing relation to said material,
   radio frequency generator means coupled for energizing said first and second conductor means in predetermined out of phase relation,
   and means responsive to the field at said third conductor means for indicating moisture in said material,
   wherein said first, second and third conductor means comprise an array which includes a said first conductor means, a said second conductor means and a said third conductor means disposed in order and in offset relation to one another, while being in spaced relation to said material,
   said first conductor means being disposed with second conductor means on either side thereof in substantially parallel relation to the path of said material, and wherein said third conductor means is disposed on the remote side of said second conductor means from said first conductor means and also in substantially parallel relation to the path of said material.

8. Apparatus for measuring the moisture content of material, said apparatus comprising:
   a first pair of conductor means disposed in facing relation to said material, said pair of conductor means being differentially coupled to one another in out of phase relationship,
   third conductor means disposed in facing relation to said material,
   and means responsive to the differential coupling as between said third conductor means and each of said pair of conductor means, including radio frequency generator means coupled to conductor means and means responsive to radio frequency energy as differentially coupled in out of phase relationship via the material,
   wherein said pair of conductor means and said third conductor means comprise an array which includes said pair of conductor means disposed in offset relation to one another and wherein said third conductor means is disposed in offset relation on the remote side of one of said pair of conductor means from the other of said pair of conductor means, said pair of conductor means and said third conductor being disposed in spaced relation to said material in substantially the same plane on the same side of said material.

* * * * *